United States Patent
Andell et al.

(10) Patent No.: US 8,219,239 B2
(45) Date of Patent: Jul. 10, 2012

(54) DENTAL UNIT WITH PROGRAMMABLE FUNCTIONS

(75) Inventors: Henri Andell, Espoo (FI); Tero Pihlajamäki, Helsinki (FI)

(73) Assignee: Planmeca Oy, Helsinki (FI)

( * ) Notice: Subject to any disclaimer, the term of this patent is extended or adjusted under 35 U.S.C. 154(b) by 296 days.

(21) Appl. No.: 12/450,227

(22) PCT Filed: Mar. 18, 2008

(86) PCT No.: PCT/FI2008/050123
§ 371 (c)(1),
(2), (4) Date: Oct. 13, 2009

(87) PCT Pub. No.: WO2008/113888
PCT Pub. Date: Sep. 25, 2008

(65) Prior Publication Data
US 2010/0092913 A1   Apr. 15, 2010

(30) Foreign Application Priority Data
Mar. 19, 2007   (FI) ..................................... 20075181

(51) Int. Cl.
*G06F 19/00* (2011.01)
*G05B 11/01* (2006.01)
*G05B 15/00* (2006.01)
*A61C 1/02* (2006.01)
*A61C 3/00* (2006.01)
*A61C 19/00* (2006.01)
*A61G 15/00* (2006.01)

(52) U.S. Cl. .............. 700/170; 700/17; 700/83; 433/28; 433/33; 433/52; 433/53; 433/101

(58) Field of Classification Search .............. 433/27–29, 433/33, 49, 52, 53, 77, 79, 80, 82, 84, 85, 433/98, 101; 700/2, 12, 17, 83, 170, 282
See application file for complete search history.

(56) References Cited

U.S. PATENT DOCUMENTS
4,382,786 A * 5/1983 Lohn et al. ..................... 433/85
(Continued)

FOREIGN PATENT DOCUMENTS
EP   0845247   3/1998
(Continued)

OTHER PUBLICATIONS
International Search Report mailed Sep. 8, 2008.

*Primary Examiner* — Crystal J Barnes-Bullock
(74) *Attorney, Agent, or Firm* — Stites & Harbison PLLC; Juan Carlos A. Marquez, Esq.

(57) ABSTRACT

Dental unit, which comprises at least one connection for at least one ancillary device, a drive-power and feed system for providing drive power or feed to said at least one ancillary device, and a control system for controlling the drive-power and feed system as well as the at least one ancillary device. For its part, the control system comprises at least one programmed function, which includes at least one predefined control operation directed to at least one ancillary device. In addition, at least one trigger is defined for each programmed function within the control system, in response to which said programmed function is performed. According to the invention, the dental unit comprises configuration means, which are arranged to receive control commands from the user in order to configure at least one programmed function and to configure said at least one programmed function according to control commands received from the user.

25 Claims, 9 Drawing Sheets

U.S. PATENT DOCUMENTS

| | | | |
|---|---|---|---|
| 4,443,195 A * | 4/1984 | Matsui | 433/84 |
| 5,538,423 A | 7/1996 | Coss et al. | |
| 5,931,669 A * | 8/1999 | Fornoff et al. | 433/28 |
| 6,470,222 B1 * | 10/2002 | Davidson et al. | 700/2 |
| 7,211,220 B2 * | 5/2007 | Castellini | 422/28 |
| 7,455,520 B2 * | 11/2008 | Sorensen et al. | 433/98 |
| 7,893,926 B2 * | 2/2011 | Nyholm | 345/173 |
| 2004/0183352 A1 | 9/2004 | Schron | |
| 2006/0127840 A1 * | 6/2006 | Fornoff et al. | 433/77 |
| 2006/0177795 A1 | 8/2006 | Sorensen et al. | |
| 2007/0026359 A1 | 2/2007 | Sorensen et al. | |
| 2010/0036535 A1 * | 2/2010 | Feine et al. | 700/282 |

FOREIGN PATENT DOCUMENTS

| | | |
|---|---|---|
| EP | 1 010 404 A2 | 12/1999 |
| EP | 1 743 594 A1 | 7/2005 |
| WO | WO 2004/084753 A1 | 3/2004 |
| WO | WO 2004/080324 A1 | 9/2004 |
| WO | WO 2005/070366 A1 | 8/2005 |
| WO | WO 2006/037862 A1 | 4/2006 |
| WO | WO 2007006804 A2 | 1/2007 |

* cited by examiner

DENTAL UNIT WITH PROGRAMMABLE FUNCTIONS

BACKGROUND OF THE INVENTION

The present invention relates to a dental unit according to the preamble of claim 1.

A dental unit is a device to which one or more ancillary devices can be attached. Typical ancillary devices are the instruments used in dental treatment, as well as control devices. The dental unit is usually arranged to feed the ancillary devices with the electricity, water, compressed air, vacuum, or mechanical power that they require. Modern dental units are generally microprocessor controlled.

Typical instruments are, for example, micromotor and turbine drills, light curers, water sprays, and similar. Typical ancillary devices also include suction devices for removing saliva and treatment by-products from the mouth. The instruments and suction devices are connected to the actual dental unit by means of hoses. The hoses of the instrument may contain water connections, an air connection and electrical wires for operating the instruments, always according to the type of instrument.

A typical control device for a dental unit is a foot control, which permits control commands to be given to the dental unit with the aid of the foot, at least during treatment operations. Foot control is more hygienic than hand-operated controls, as there is then no need to touch the control surfaces in the middle of treatment. In addition, there is typically at least one hand control in a dental unit, such as a keypad or a touch surface. Dental units equipped with touch screens are also known. Other control alternatives may certainly also be used, e.g. voice control based on speech recognition.

A patient chair is also typically attached to a dental unit, in which case the patient chair can also be controlled via the control devices of the dental unit. Other typical ancillary devices are an operation light and a flushing-water system, for example.

WO 2004/084753 discloses a dental unit equipped with a graphical user interface.

WO 2006/037862 presents a dental unit, which can be connected to a computer over a data communications link.

WO 2005/070366 discloses a computer-controlled dental unit comprising a graphical user interface and a data communications connection.

Modern dental units offer dentists several advanced functions. In modern dental units, there has been even predefined more advanced functions the performing of which is linked to several control functions, which are directed to the ancillary devices of the dental unit and/or to the dental unit's own systems. The defined functions may include, for example, functions programmed for specific treatment operations. Such a function may comprise, for example, guiding the patient chair to a proper position, switching the operation light on/off, and setting the instruments to a proper operating status. In the most advanced dental units, the user is given an opportunity to define parameters, such as positions of a patient chair or operating times, for the control operations included in the functions.

Diverse and advanced functions in a dental unit facilitate dentist's work, because the dental unit can be used to perform versatile operations. On the other hand, the versatile range of functions requires a considerably more complex user interface and thus also makes it more difficult to use the dental unit. A more complex user interface is not always as clear as a user interface containing only simple manual adjustments and, during treatment, the dentist or the dental assistant may be unaware of some of the prevailing settings of the dental unit. Thus, on the other hand, the diversification of dental unit's functions has created new kinds of possibilities for errors in the use of a dental unit.

BRIEF SUMMARY OF THE INVENTION

The invention is intended to make the using a dental unit more flexible and safe, at least during treatment operations.

The invention is based on implementing a configuration function in a dental unit, with the aid of which the user can not only configure the parameters contained in the programmed functions but also the programmed functions themselves. Examples of configuring of a programmed function are removal of a control operation from a programmed function, addition of a control operation to a programmed function, addition of a new programmed function, creation of a new programmed function by combining previously programmed functions, removal of an entire programmed function.

More specifically, the dental unit according to the invention is characterized by what is stated in the characterizing portion of claim 1.

With the aid of the invention, the flexibility of the use of a dental unit and its safety during a treatment operation can be improved.

The invention makes it possible e.g. for the user of a dental unit to himself, prior to a treatment operation, program functions he considers suitable, e.g. in addition to the functions preprogrammed at the factory. This will reduce the possibility for making an error upon use, because control of the dental unit optimally relating to the treatment procedure cannot be forgotten as the control system of the dental unit itself takes care of the sub-functions. The possibility for an error upon use is reduced also through that the control commands relating to the treatment operation can be entered into a dental unit by taking one's time prior to the treatment operation. This makes it easier to carefully check the parameters and settings of the programmed functions relating to the treatment operation as a sub-function.

The possibility to configure programmed functions can thus improve reliability, safety, and quality of the treatment. In addition, combining of operations to be performed through a single control command reduces the number of work stages to be performed during treatment and thus makes work more flexible.

In known dental units containing programmed functions, when the treatment case or patient changes, it may have been necessary to run through the settings of the functions with the aid of a checklist to ensure that all of the most important settings are correct. This takes time and exposes one to lapses of memory. According to a preferred embodiment, functions and function-totalities contained in entire dental treatment operations can be programmed into the dental unit such that these functions and function-totalities are easily available with the aid of simple control commands. In a preferred embodiment, also the user interface of a dental unit can be configured to an optimal state for individual dental treatment operations according to the wishes of the care personnel. For the same dental treatment operation, several different versions can be defined for the dental unit, too, and they can be named according to the purpose of use of the versions, for example. Thus, the dentist can separately program into the dental unit a specific dental treatment operation e.g. for patients of different sizes, or for problematic treatment cases of different degrees. This will further improve flexibility and reliability of the treatment.

BRIEF DESCRIPTION OF THE DRAWINGS

In the following, the invention is contemplated with the aid of examples and with reference to the accompanying drawings.

DETAILED DESCRIPTION OF THE INVENTION

The dental unit of the example comprises connections for ancillary devices, as well as a drive-power and feed system for providing drive power or feed to the ancillary devices. The ancillary devices are, for example, instruments, control devices, a patient chair, an operation light, a suction system, a flushing-water system, and a display. The dental unit also comprises a drive-power and feed-system for providing drive power or feed to the ancillary devices. The drive power or feed provided comprises at least one of the group: electricity, water, compressed air, vacuum, mechanical power, and light.

In addition, the dental unit comprises a control system for controlling the aforementioned. The control system comprises at least one programmed function, which contains at least one predefined control function being directed to at least one ancillary device, and at least one trigger is defined in the control system for each programmed function in response to which said programmed function is performed. Typically, there are tens and even hundreds or thousands of programmed functions. Some of the functions are preprogrammed at the factory and some of the functions are denied in the device as fixed in such a way that, if desired, they can be reinstated as original default functions.

The configuration means of the dental unit is arranged to receive control from the user in order to configure the programmed functions and to configure the functions according to the control received from the user. This control can be received from any control device, but usually the more complex programming takes place through a key surface. In the programming, the triggers relating to the functions are also defined. As stated above, it is preferable to be able to remove and add programmed functions and to configure their contents in such a way that selected control operations are removed from or added to the function. In addition, surely, it is possible to define the parameters of the control operations in the same way as previously.

A control operation can be, for example, switching on an operation light, switching off an operation light, dimming an operation light, controlling a motor of a patient chair in order to steer the chair into a desired position, feeding of power to an instrument, feeding of water to an instrument, feeding of compressed air or vacuum to an instrument, filling a mug with water, flushing a spit bowl, switching a cooling mist for an instrument on or off, or sending for a dental assistant. By their nature, the control operations are simple basic control commands in the software of the dental unit, or very simple combinations of them.

By combining basic control commands it is possible to realize simple programmed functions, such as setting a power limit for an instrument, setting an operating status of an instrument, adjusting an operating status of an instrument, setting an operating status (view) of a display, adjusting cooling mist of an instrument, setting the operating time for suction, defining a control command for a control device, or defining control commands linked to selectors of a foot control.

However, the programmed functions may also contain complex and extensive combinations of basic control commands, or of other programmed commands. Programmed functions, which themselves include at least one programmed function, can also be called combination functions. Generally, a programmed function contains a combination of two or more control operations and a definition for whether the control operations are to be performed e.g. consecutively or simultaneously. The control operations may be control operations mentioned above or other control operations the dental unit makes possible.

Thus, in the programmed functions, one can also refer to another programmed function. In this case, the programmed function to be performed activates the other programmed function being defined to be a part thereof, which in turn activates the programmed functions or simpler control operations being parts of it. By this way, changes in the settings of the control operations and the programmed functions are taken to use also in the more extensive functions exploiting the aforementioned control operations and programmed functions.

In a preferred embodiment, the user himself may define icons onto a display of a graphical user interface, which icons point to the combination functions defined by the user. In this way, the user can steer the dental unit to perform a combination function by simply selecting an icon corresponding the combination function with the aid of, for example, a foot control or a touch screen.

A programmed function may also include control operations or programmed functions which are to be conditionally performed. In such case, when the programmed function is performed, a check is made as to whether the condition is met and the conditional control operation or the programmed function will be performed only if the predefined condition is met. The condition may be, for example, a specific operating status of a specific ancillary device, a specific control received from the user, or passage of a predefined period of time from a predefined event. The contents of a programmed function can also be defined to be conditional so that a specific parameter or specific parameters will have a first value when a first condition is met, and a second value when a second condition is met or when the first condition is not met.

Further, it is possible to set performance of an entire programmed function to be conditional.

The user may define conditions through a configuring function.

In the following, some possible programmed functions containing aforementioned combinations will be described.

A programmed function can thus contain, for example, a control operation for steering a patient chair to a predefined position and one or more other controls combined with this. The other control can be, for example, control of an operation light and setting of the operating status of instruments.

One programmed function can be, for example, rinsing the patient's mouth, which function includes filling of a mug with water, moving of the patient chair to a rinsing position. Termination of the function may be incorporated in the same function, which includes flushing of the spit bowl and moving of the chair to a getting-off or to an operation position. The termination may also be realized as a separate function.

One programmed function includes driving of the chair to an exit position and switching off the light.

One programmed function includes driving the chair to an exit position, flushing of the bowl, switching off the light and sending for the assistant.

One programmed function includes setting of the operating status of at least two instruments for a selected treatment operation.

One programmed function includes setting of the operating status of a display and at least one instrument for a selected treatment operation.

One programmed function includes setting of the operating status of at least one instrument and moving of the patient chair to a predetermined position for a selected treatment operation.

One programmed function includes setting of the operating status of at least one instrument and defining of control commands relating to selectors of a foot control for a selected treatment operation.

One programmed function includes defining of control commands of a display and of those incorporated into the selectors of a foot control.

One programmed function includes defining of an icon and/or text to be shown on a display relating to the programmed function.

One example of a programmed function to be conditionally performed is flushing of an instrument. This can be set to be conditional e.g. such that flushing is performed if a specific time, such as one day, has passed since the previous flushing.

In one embodiment, the dental unit comprises a display and the control system is arranged to show on a display a view, which contains symbols, such as icons, numbers, and/or text. The control system is also arranged to receive control commands, relating to the symbols, from a control device or control devices connectable with the dental unit. Programmed functions may be incorporated into the aforementioned symbols. Control commands to be received from a control device act as triggers to these programmed functions.

The dental unit can also include such programmed functions, which control the contents of the view shown on a display.

In one embodiment, the view shown on a display comprises at least one area within which a menu for selecting an operating status is shown, and at least one area within which symbols for giving control commands to be directed to ancillary devices are shown. In a preferred embodiment, such a display is controlled by means of a foot control comprising selectors, and the view shown on the display comprises one area for each selector. In addition, the view typically comprises one or more areas, which can be used, for example, for showing information.

A menu typically contains several sub-menus and, thus, the view shown on a display only contains some of the menus and icons. The menus and symbols to be shown on a display at a time are selected on the basis of control and status information received from the control system. These menus and icons shown on the display may also be configured by the user.

In the following, some conceivable functionalities are presented at length.

Logging On

Supposing there are several users of the dental unit, a logon view is shown on the display. The users may be, for example, dentists, dental assistants, or oral hygienists. The intent of the function is to make available user's personal settings when the dental unit is set into the treatment mode.

Logging on takes place by selecting a proper user from the user menu in the logon view. The menu shows the users which are recorded on an internal memory device of the dental unit, on a USB flash drive connected to the dental unit, on an external database available to the dental unit, or some other suitable memory device.

The dental unit is arranged to monitor its USB port and to display in a menu preferably the first users on the USB flash drive when a USB flash drive is placed in the USB port. The dental unit can also be programmed in such a way that, when a USB flash drive is placed in the USB port, only the users defined on the USB flash drive are shown in the menu. The other user data can be accessed through a separate selection key and by removing the USB flash drive from the USB port. It is possible to use a similar procedure with other memory devices carried by the user as well.

The users in the memory of the dental unit and in a possible database accessible through a data network are preferably displayed in alphabetical order, or through a menu with an alphabetical index if there are a considerable number of users.

The logon function also includes a possibility to logon to the dental unit as a guest. In that case, the dental unit is controlled on the basis of the default settings and the more advanced programmed functions will not be available.

The user can be required to enter a security code in connection with logging on.

After a successful logon, the microprocessor of the dental unit downloads the user profile from a memory device for its use, the user profile containing user specific settings. The user who has logged on can edit his own user-specific settings and record them back into the user profile on the memory device the user profile was retrieved from. The user profile can also be copied onto another memory device.

The user-specific user profile of this kind may contain settings, control-operation parameters and entire programmed functions programmed by the user.

Display

Figure 1A:
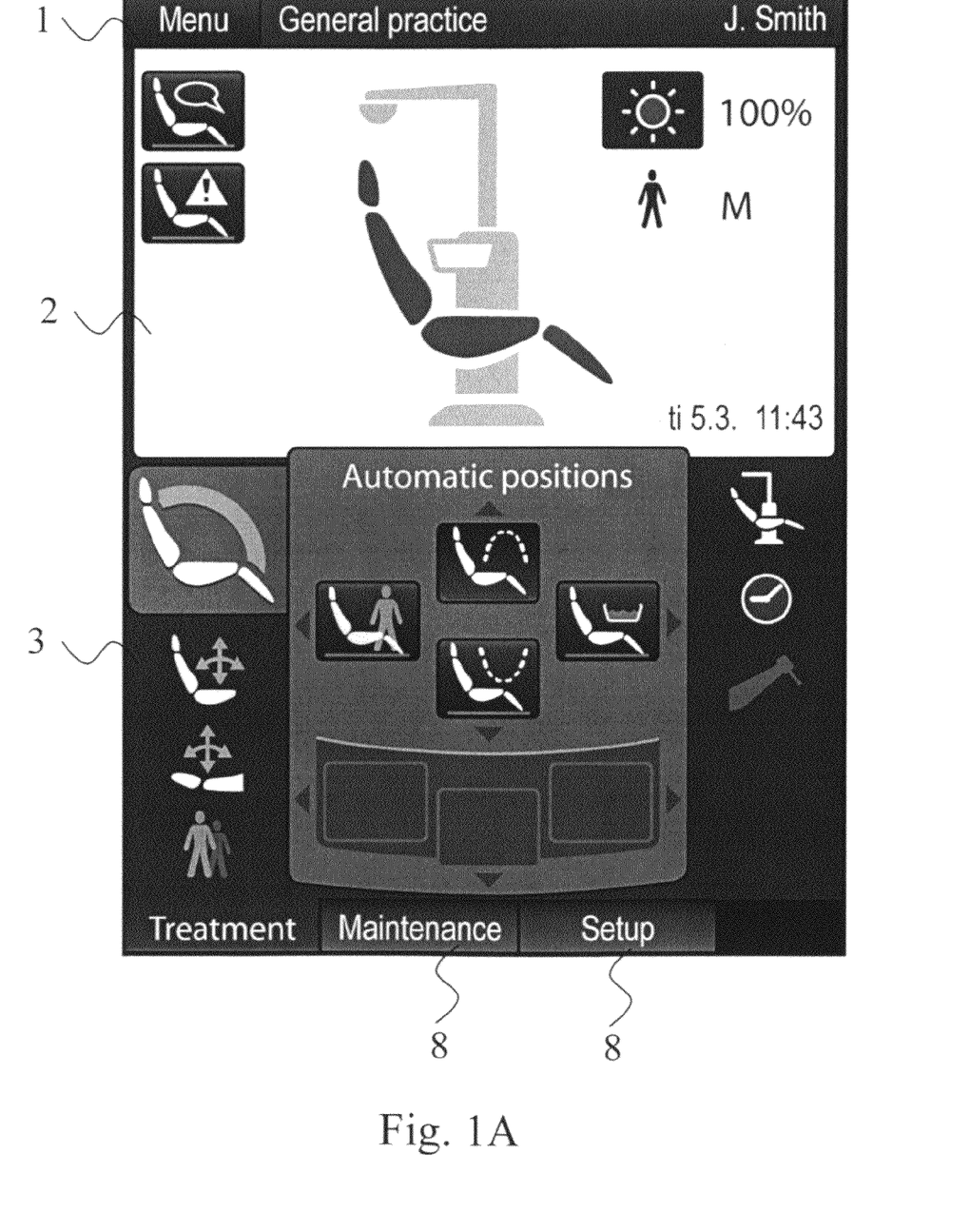
FIG. 1A shows an example of one possible view, which is shown on a display of a dental unit according one embodiment.
Figure 1B:
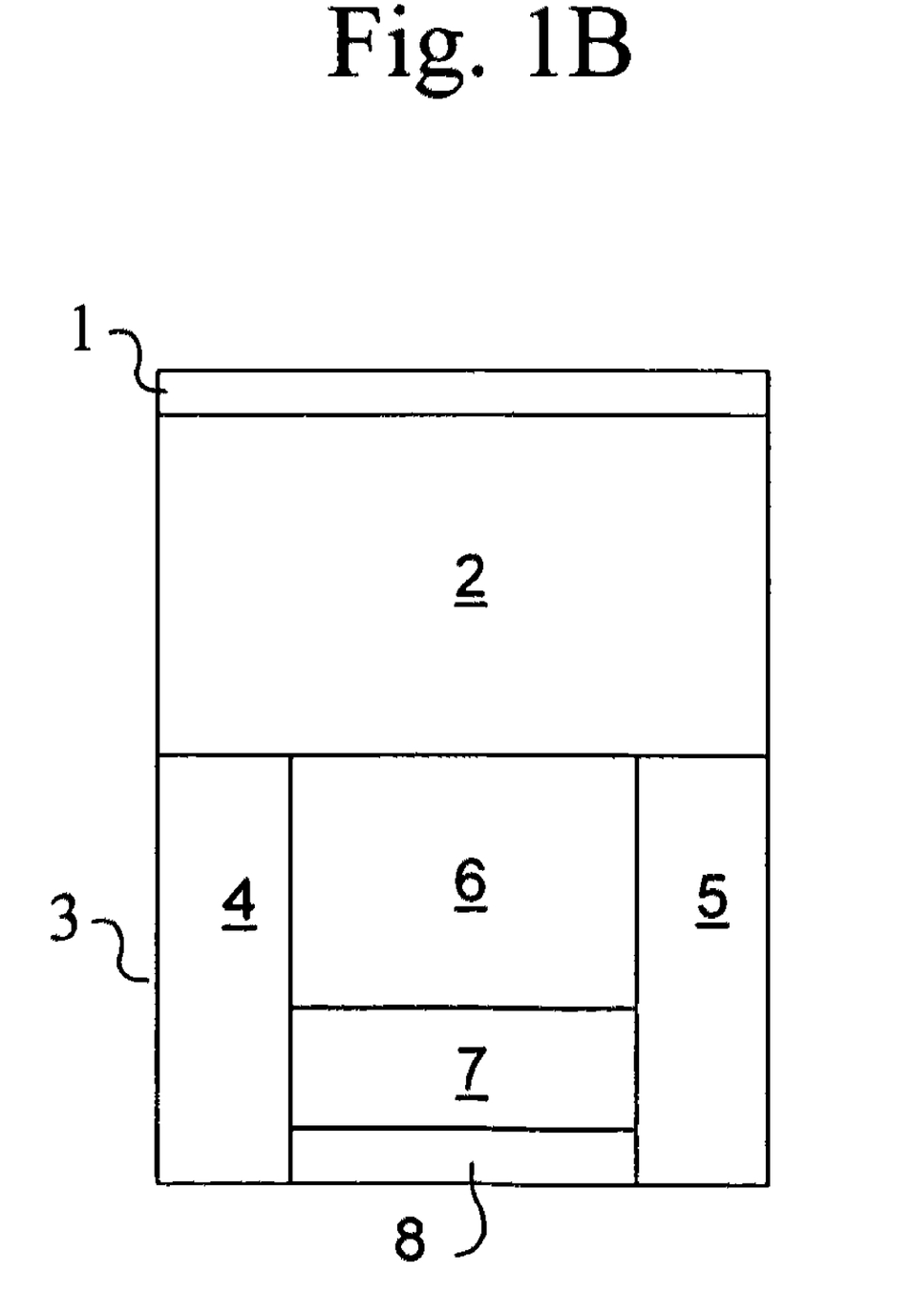
FIG. 1B shows schematically the display fields of the display of FIG. 1A.

FIG. 1A shows the basic view shown on the display in treatment mode. In different treatment and other use cases, the views will naturally differ from that shown in FIG. 1A and the basic view of the treatment mode, too, can be configured user-specifically. However, FIG. 1A is very suitable for illustrating advantageous properties of a graphical user interface of this embodiment. FIG. 1B shows schematically the same view divided in parts.

The views shown on the display comprise a header bar 1 at the upper edge of the display, through which it is possible to go to more extensive menus, such as for performing more advanced configuration and programming functions. This menu is most generally used through a keypad or some other manual control.

Below the header bar 1 there is an information panel 2 on which information is displayed regarded being important in the use case of the dental unit in question. For each treatment case, the dental unit includes an information view with default contents to be displayed on the information panel 2. In a preferred embodiment, the user may set the contents of each information view through a configuration function.

The lower half of the display shows a control panel 3, with the aid of which the user can use the functions of the dental unit, e.g. control the patient chair, edit settings, use a timer, and control instruments. Each function is linked to an icon shown on the control panel. The function is initiated or performed in response to a selection of the icon. The display being a touchscreen, user's control can be received through the display. Control directed to the functions indicated by the icons can also be received through a foot control, in a manner to be described later in greater detail. Thus, all of the functions shown on the control panel 3 are also available through the foot control.

The control panel 3 is divided into five parts. These parts are a left-hand menu 4, a right-hand menu 5, upper control icons 6, lower control icons 7, as well as maintenance and setup icons 8 on the lower edge of the display.

The view shown on the control panel 3, too, is operating-state-specific and can be configured by the user.

The parts of the control panel are linked to each other in such a way that, with the aid of the left-hand and right-hand menus 4 and 5, it is possible to select the function or function group to be used, in which case the control icons of the selected function or function group are shown on the upper and lower control icons 6 and 7. In the same way, also the view to be shown on the information panel 2 is selected, which view is thus also set to a desired state with the aid of the left-hand and right-hand menus 4 and 5. The icons shown on the menus 4 and 5 are shown in either an idle status or an active status in such a way that only one of the icons can be in an active status at any one time. The idle status and the active status can be differentiated e.g. with the aid of the colour of the icon. The left-hand and the right-hand menus 4 and 5 are preferably linked together in such a way that at a time, only on one of the menus 4 or 5 an icon can be in an active status.

Foot Control

Figure 2A:
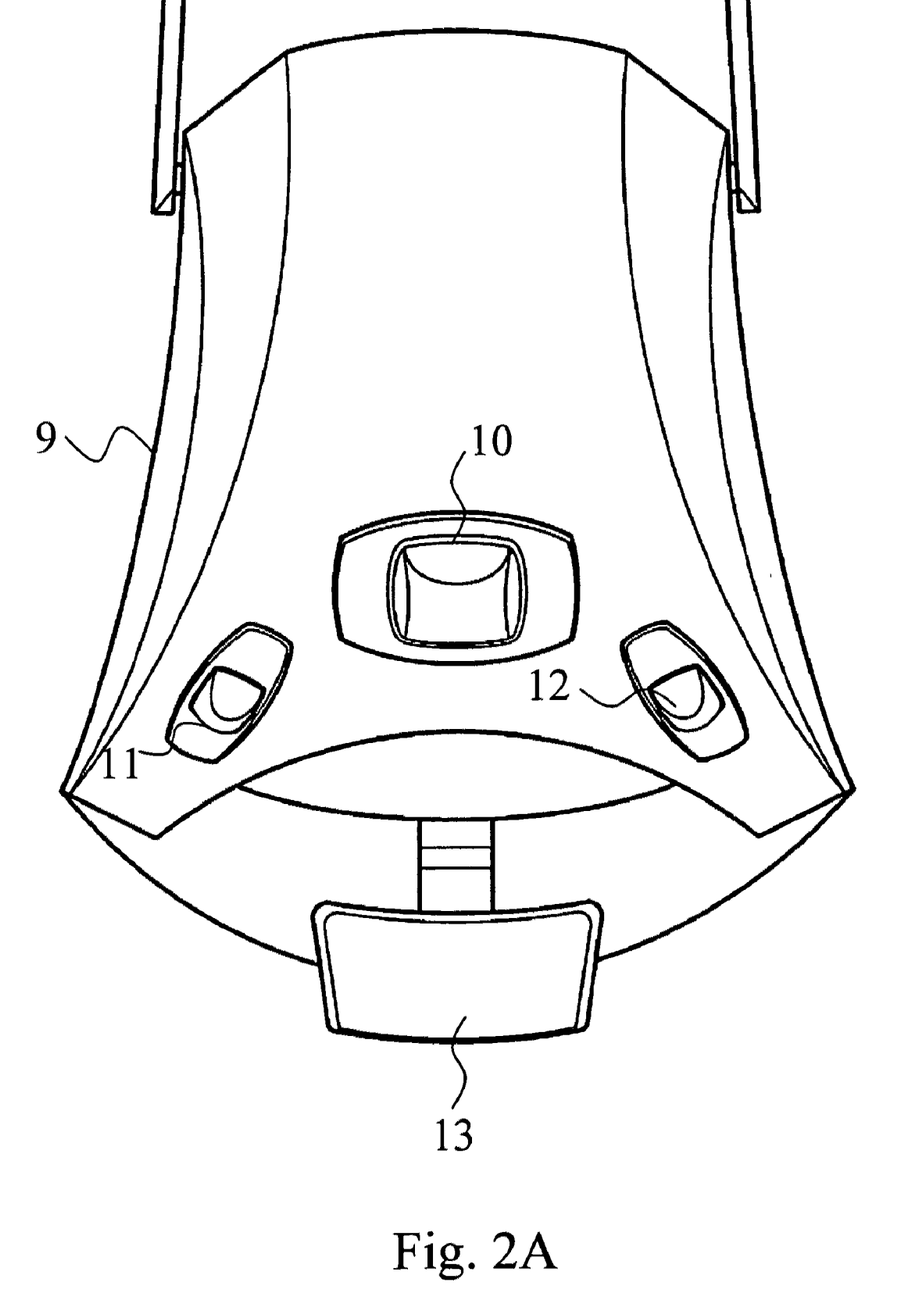
FIG. 2A shows a schematic top view of a foot control, which can be connected to a dental unit according to one embodiment.

FIG. 2A shows a foot control 9. The foot control 9 comprises a centre selector 10, a left selector 11, a right selector 12, and a pedal 13. The centre selector 10 can be guided with a foot forwards, backwards, to the left, and to the right. The left and the right selectors 11 and 12 can be guided with a foot forwards and backwards. The pedal 13 can be pressed downwards and guided to the left and to the right.

A control command can be linked to each of the control movements described above. In the present embodiment, this is done through a graphical user interface shown on the display shown by FIGS. 1A and 1B. Then, it is possible to receive control commands through the foot control relating to use-case requirements and, if desired, also to user-specific menu views and the icons shown therein. Trough the foot control, it is thus possible to use the advanced functions of the dental unit.

Figure 2B:
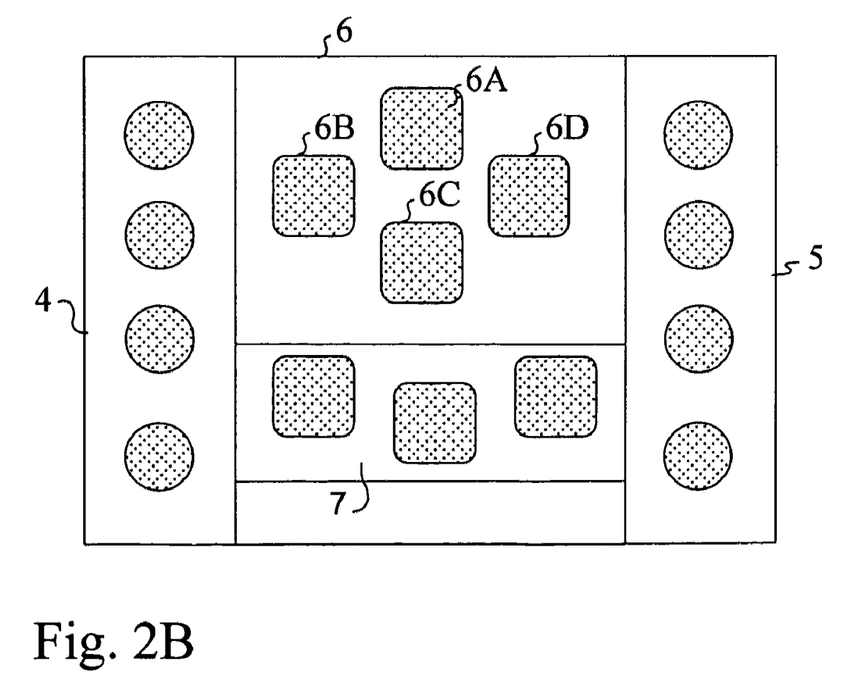
FIG. 2B shows in greater detail a schematic view of a part of the view of FIG. 1B.

In a preferred embodiment, the selectors of the foot control 9 are linked to the graphical user interface in a manner that will be described in the following, with reference to FIG. 2B. FIG. 2B is a partial view of FIG. 1B, in such a way that FIG. 2B shows only the control panel 3 of the display and, particularly, its left-hand menu 4, right-hand menu 5, upper control icons 6 and lower control icons 7. In this example, the icons of the menus 4 and 5 are shown by circular symbols and the control icons 6 and 7 by rounded squares.

In a preferred embodiment, the left-hand menu 4 of the display can be controlled using the left selector 11. The control is preferably implemented in such a way that pushing the left selector 11 forwards or backwards causes transition of one icon (and thus its related function) in the left-hand menu 4 to an active status. Steering the selector 11 forwards causes an upwards movement in the menu in such a way that when one icon is in the active status, based on this steering the active status is transferred to the next icon above. Correspondingly, steering the left selector 11 backwards causes transfer of the active status downwards in the left-hand menu 4. Should the highest or lowest icon be reached by the control, the active status will correspondingly transfer to the lowest or highest icon.

In a preferred embodiment, with the aid of the right selector 12, the right-hand menu 5 of the display is controlled in a manner corresponding entirely to that depicted above in connection with the left selector 11 and menu 4.

In a preferred embodiment, the upper control icons 6 are controlled with the aid of the centre selector 10. This is preferably implemented in such a way that pushing the centre selector 10 forwards means selecting the uppermost control icon 6A, pushing the centre selector 10 to the left means selecting the left-hand control icon 6B, pushing the centre selector 10 backwards means selecting the lowest control icon 6C, and pushing the centre selector 10 to the right means selecting the right-hand control icon 6D. In response to the selection of an icon, the dental unit performs the control operation or programmed function linked to the icon.

In a preferred embodiment, the lower control icons 7 are controlled with the aid of the pedal 13 in a manner corresponding to that described in connection with the centre selector 10 and the icons 6. Pressing on the pedal and guiding it to the left and right thus represents, correspondingly, selection of the centre, the left-hand, and the right-hand icons. The control operation or programmed function linked to the icon is performed in response to the selection of the icon.

The division of the views of the display into parts depicted by the preferred embodiment, and control of these parts by the foot control, creates a user interface that is illustrative and easy to learn.

Instrument Console

The user interface and the display can also be controlled with the aid of an instrument console. The instrument console comprises locations in which the instruments are placed when they are not in use. When an instrument is lifted out of the console, the dental unit detects the initiation of use of the instrument and takes the instrument into the operating status. When the instrument is put back to the console, the dental unit returns the instrument into the idle status. In a preferred embodiment, this control information is also linked to the control of the graphical user interface in such a way that taking an instrument into the active status also affects the view shown on the display.

Quick-Save Function

The user interface is also preferably equipped with a quick-save function, with the aid of which the state or settings of the controlled ancillary devices can be easily recorded in a memory. This can be implemented e.g. by showing quick-programming icons on the display and performing recording in response to selection of the quick-programming icon when the icon is in the quick-programming status. Upon this, the recorded settings are linked to the quick-programming icon so that the ancillary devices may be taken to the recorded state by selecting the quick-programming icon when the icon is in the control state. Switching between the quick-programming status and the control status may be performed by manual selection, or the control system may automatically change the status in response to the operating status of the system or to the changes in it. Selection between the quick-programming status and the control status can also be set to be carried out on the basis of the manner of selection of the icon in such a way, for example, that a longer-lasting selection signal realizes saving and a shorter-lasting signal guides the system to a previously recorded state.

Views

There are quite many possible views that can be shown on the display in the exemplary dental unit. In the following, some views are presented which illustrate the diverse possibilities provided by the user interface according to a preferred embodiment.

Figure 3:
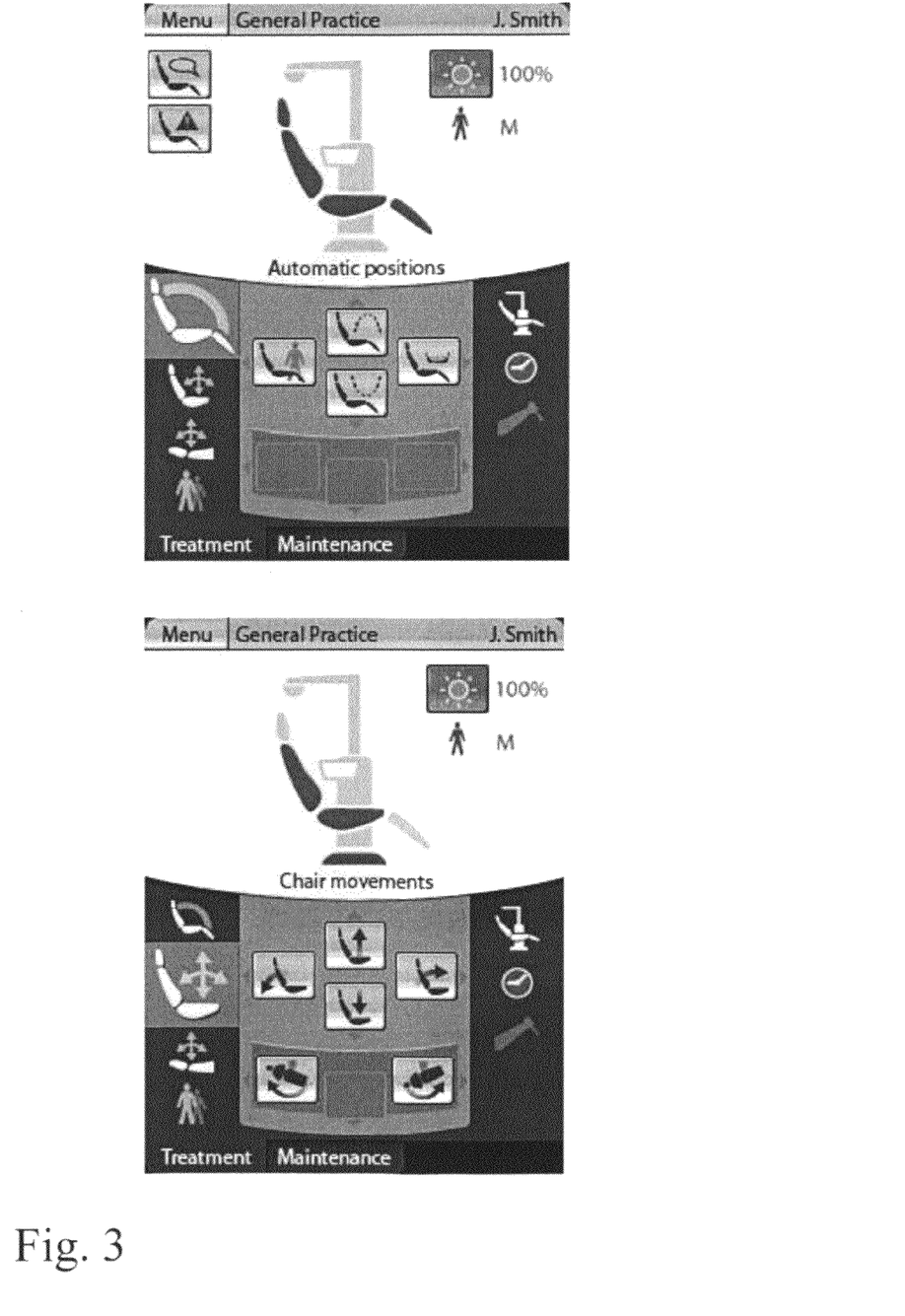
FIG. 3 shows two examples of possible views.

FIG. 3 shows two examples of the numerous possible views relating to control of a patient chair.

Figure 4:
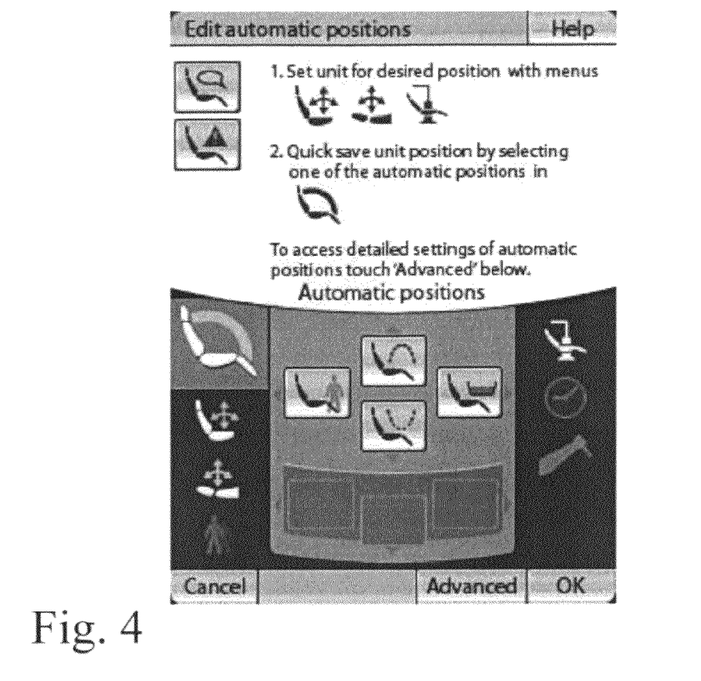
FIG. 4 shows one possible configuration view for positions of a patient chair.

FIG. 4 shows one possible view for configuring positions of a patient chair in the basic programming mode.

Figure 5:
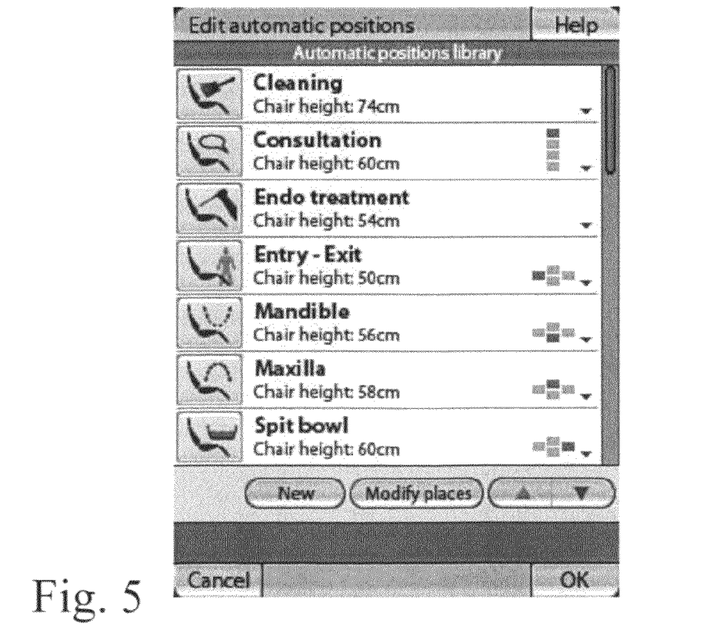
FIG. 5 shows a second possible configuration menu for positions of a patient chair.

FIG. 5 shows one possible view for configuring positions of a patient chair in the expanded programming mode. The view includes a menu.

Figure 6:
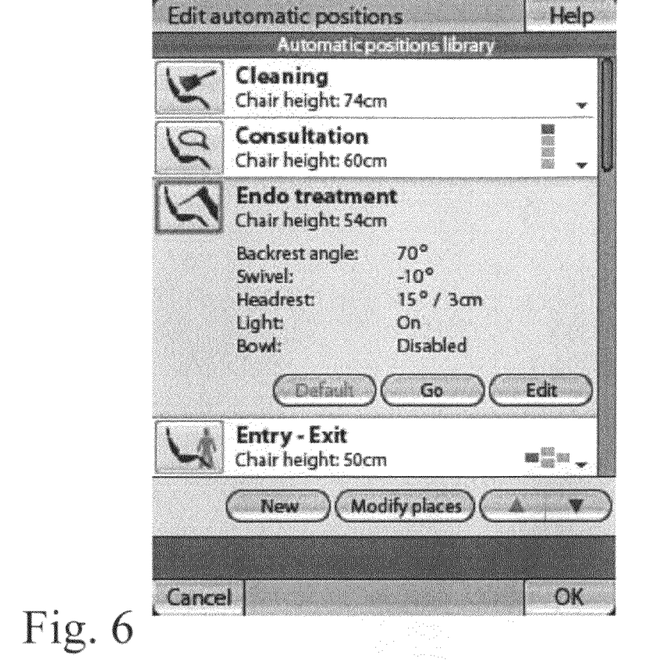
FIG. 6 shows one possible view with a sub-menu of the menu of FIG. 5 open.

FIG. 6 shows one possible configuring view in which one sub-menu in the menu of FIG. 5 has been opened.

Figure 7:
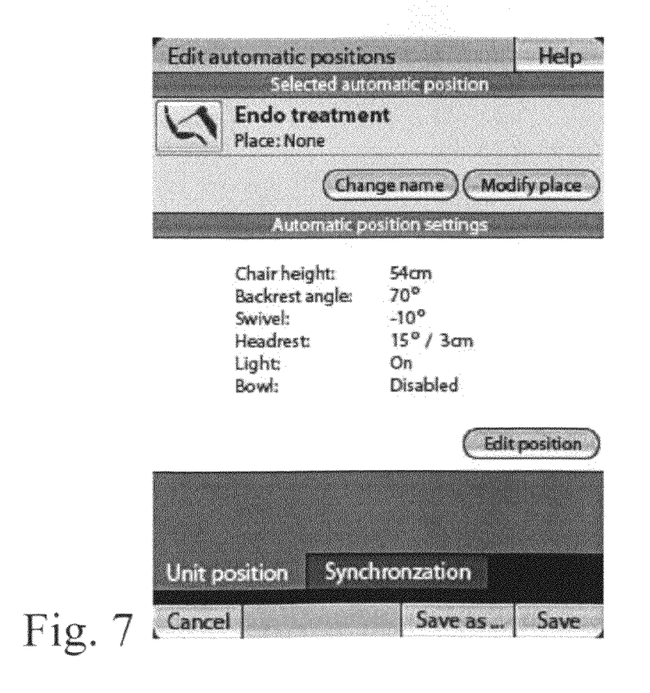
FIG. 7 shows one possible view for configuring parameters of the sub-menu of FIG. 6.

FIG. 7 shows one possible configuring view, through which it is possible to edit the parameters shown in the sub-menu of FIG. 6.

Figure 8:
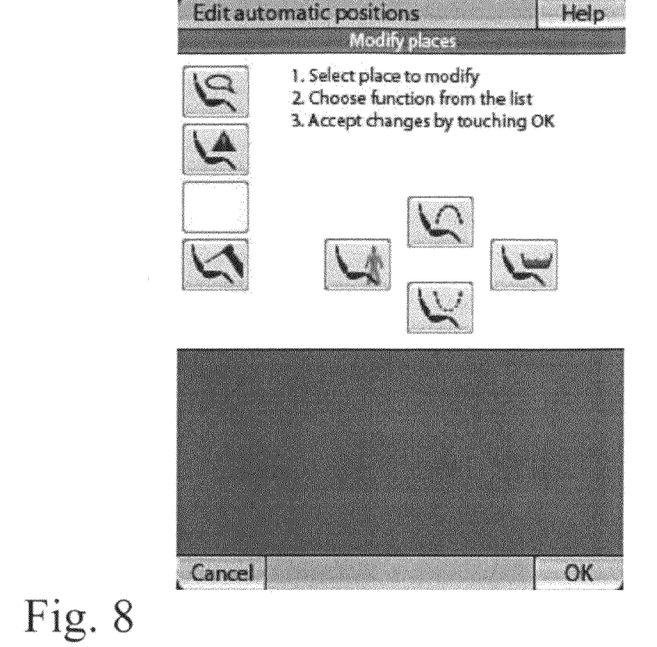
FIG. 8 shows one possible view, through which a configured function can be directed to a desired icon shown on a display.

FIG. 8 shows one possible view through which a configured function can be directed to a desired icon being shown on the display.

Figure 9:
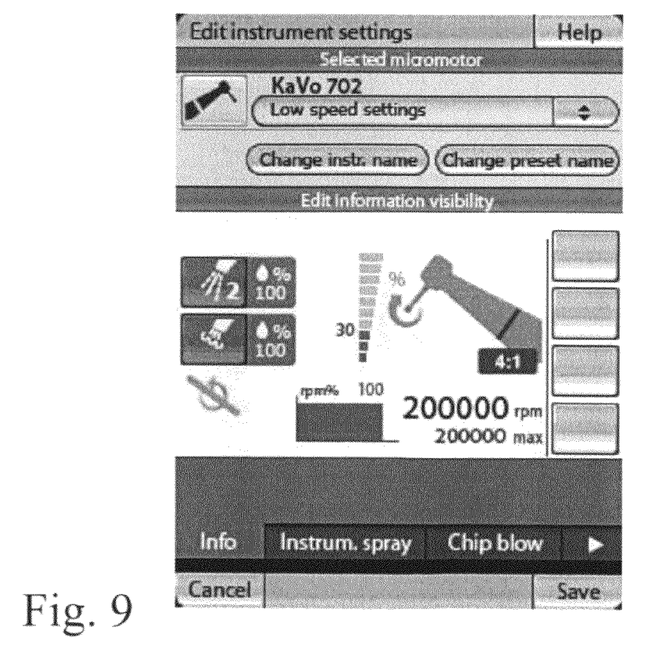
FIG. 9 shows one possible configuring view for display settings of an instrument.

FIG. 9 shows one possible view for editing settings of an instrument, through which it is possible to edit data of the instrument shown on the information panel 2 during use, i.e. to select, for instance, which parameter values will appear on the information panel 2.

Figure 10:
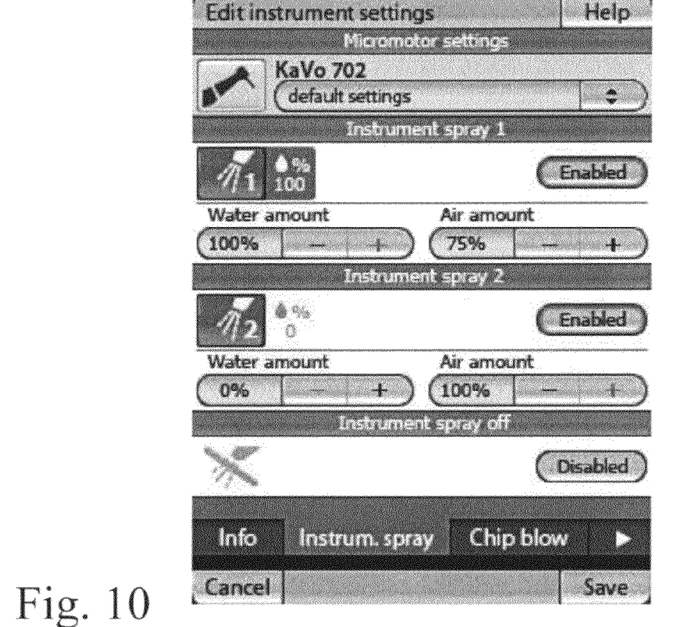
FIG. 10 shows one possible configuration view for instrument settings.
Figure 11:
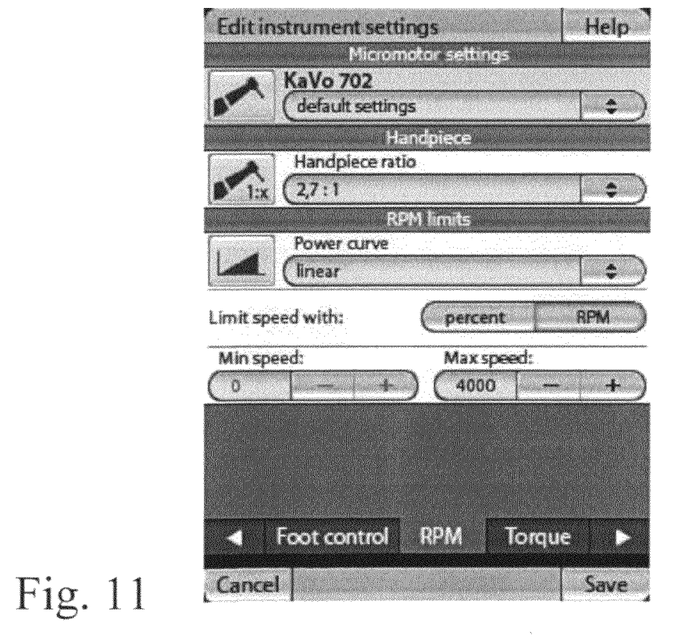
FIG. 11 shows a second possible configuration view for instrument settings.

FIGS. 10 and 11 show two different examples of a configuring view for the settings of an instrument, through which setting of the instrument can be configured.

On the basis of the examples described above, it will be obvious that within the scope of the invention, numerous solutions differing from the embodiments described above can be implemented. Thus, it is not intended to restrict the invention to concern only the examples described above, but instead the patent protection shall be considered to the full extent of the accompanying claims.

The invention claimed is:

1. A dental unit, comprising
at least one connection for at least one ancillary device,
a drive-power and feed system for providing drive power or feed to said at least one ancillary device,
a control system for controlling the drive-power and feed system as well as said at least one ancillary device, which control system comprises at least one programmed function, which includes at least one predefined control operation directed to at least one ancillary device including at least one parameter, and in which control system at least one trigger is defined for each programmed function, in response to which said programmed function is to be performed,
a means adapted to receive control from a user to change a value of a parameter included in said at least one control operation,
characterized in that the dental unit comprises a configuration means, which is arranged to receive control commands from the user for modifying said at least one programmed function and to modify said at least one programmed function according to the control received from the user, which modification of the programmed function comprises at least one function selected from the group consisting of (i) removal of a control operation from a programmed function, addition of a control operation to a programmed function, (ii) addition of a new programmed function, (iii) creation of a new programmed function by combining previously programmed functions, and (iv) removal of an entire programmed function.

2. The dental unit according to claim 1, characterized in that the configuration means is arranged to add a new programmed function to the control system.

3. The dental unit according to claim 1, characterized in that at least one programmed function includes a condition defined for performing of the function and the control system is arranged to perform said programmed function only if the condition defined for performing the function is met.

4. The dental unit according to claim 1, characterized in that at least one programmed function includes at least one control operation or another programmed function for performing of which a condition has been defined and the control system is arranged to perform, when performing said at least one programmed function, said at least one control operation or another programmed function only if the condition defined for the performance of said control operation or another programmed function is met.

5. The dental unit according to claim 1, characterized in that the configuration means includes a function for linking programmed functions the dental unit contains together to form a combination function.

6. The dental unit according to claim 5, characterized in that the configuration means comprise a function for defining a trigger relating to the combination function and the dental unit is arranged to perform the programmed functions linked to form a combination function in response to the trigger relating to the combination function.

7. The dental unit according to claim 6, characterized in that the dental unit comprises a display on which icons are shown, and the configuration means includes a function for selecting an icon and for defining it to be a trigger relating to a combination function, whereby the dental unit can be guided to perform the combination function through the selected icon.

8. The dental unit according to claim 1, characterized in that the dental unit contains at least one function permanently programmed into the dental unit and the configuration means is arranged to create a new programmed function by using as a base the function preprogrammed at a factory.

9. The dental unit according to claim 8, characterized in that the configuration means is arranged to provide the user with the possibility to remove control operations, add control operations, and/or alter the settings of control operations upon creation of said new programmed function.

10. The dental unit according to claim 1, characterized in that the configuration means is arranged to alter the contents of a programmed function and/or the trigger defined for a function.

11. The dental unit according to claim 1, characterized in that the dental unit contains a set of said programmed functions in such a way that at least one of the programmed functions contains at least two control operations.

12. The dental unit according to claim 11, characterized in that the control system is arranged to perform a programmed function by activating the control operations contained in the function.

13. The dental unit according to claim 1, characterized in that the configuration means is arranged to add to the control system a programmed combination function, which contains a first programmed function and at least one control operation or a second programmed function, and in which the control system is arranged to perform said combination function in such a way that, when performing the combination function, each programmed function or control operation included in the combination function is activated and, when the activated function is a programmed function, the programmed function activated is performed by activating the control operations or programmed functions included therein.

14. The dental unit according to claim 1, characterized in that the ancillary devices include at least one control device.

15. The dental unit according to claim 14, characterized in that at least one control device is a foot control.

16. The dental unit according to claim 14, characterized in that at least one control device is a touch surface arranged in connection with a graphical user interface.

17. The dental unit according to claim 14, characterized in that at least one trigger defined for at least one programmed function is a control command received from a control device.

18. The dental unit according to claim 1, characterized in that the dental unit comprises a display and the control system is arranged to show a view on the display, which view contains icons, numbers, text, and/or other symbols and the control system is arranged to take control commands relating to the symbols from a control device connectable to the dental unit.

19. The dental unit according to claim 18, characterized in that a programmed function, as a trigger of which acts a control command received from the control device, is attached to at least one of said symbols.

20. The dental unit according to claim 18, characterized in that at least one programmed function controls the contents of the view shown on a display.

21. The dental unit according to claim 18, characterized in that the view shown on a display comprises at least one area in which a menu is shown for selecting an operation state, and at least one area in which symbols are shown for giving control commands directed to the ancillary devices.

22. The dental unit according to claim 21, characterized in that a foot control comprising selectors is connectable to the dental unit and a view shown on a display comprises one area for each selector.

23. The dental unit according to claim 18, characterized in that the control system comprises a set of symbols for giving control commands directed to the ancillary devices, and the control system is arranged to select from the set of symbols a sub-set of symbols to be shown on the display.

24. The dental unit according to claim 18, characterized in that the control system comprises a set of menus for selecting the operating state and the control system is arranged to select from the set of menus the menu or menus to be shown on the display at any one time.

25. The dental unit according to claim 18, characterized in that the configuration means is arranged to provide the user of the dental unit with a configuration function, which enables configuring menus and symbols user-specifically.

* * * * *